(12) United States Patent
Mendoza et al.

(10) Patent No.: US 7,771,691 B2
(45) Date of Patent: Aug. 10, 2010

(54) COMPOUND AND METHOD FOR THE SELECTIVE EXTRACTION OF HIGHER FULLERENES FROM MIXTURES OF FULLERENES

(75) Inventors: Javier de Mendoza, Taaragona (ES); Elisa Huerta Martinez, Tarragona (ES); Gerald Metselaar, Tarragona (ES)

(73) Assignee: Institut Catala D'Investigacio Quimica, Tarragona (ES)

( * ) Notice: Subject to any disclaimer, the term of this patent is extended or adjusted under 35 U.S.C. 154(b) by 575 days.

(21) Appl. No.: 11/782,498

(22) Filed: Jul. 24, 2007

(65) Prior Publication Data

US 2008/0025904 A1 Jan. 31, 2008

Related U.S. Application Data

(60) Provisional application No. 60/833,069, filed on Jul. 25, 2006.

(51) Int. Cl.
*B01J 19/08* (2006.01)
(52) U.S. Cl. .......................... 423/445 B; 423/DIG. 39; 423/DIG. 40
(58) Field of Classification Search ............. 423/445 B, 423/DIG. 39, DIG. 40
See application file for complete search history.

(56) References Cited

OTHER PUBLICATIONS

A. Hirsch, M. Brettreich, "Fullerenes, Chemistry and Reactions" (Wiley-VCH, Weinheim, 2005).
D. H. Parker et al., "Fullerenes and Giant Fullerenes: Synthesis, Separation, and Mass Spectrometric Characterization", Carbon 30, 1167 (1992).
W. A. Scrivens, P. V. Bedworth, J. M. Tour, "Purification of Gram Quantities of C60, A new Inexpensive and Facile Method", J. Am. Chem. Soc. 114, 7917 (1992).
I. L. Isaacs, A. Wehrsig, F. Diederich, "Improved Purification of C60 and Formation of σ- and π-Homoaromatic Methano-Bridged Fullerenes by Reaction with Alkyl Diazoacetates", Helv. Chim. Acta 76, 1231 (1993).
N. Komatsu, T. Ohe, K. Matsushige, "A Highly Improved Method for Purification of Fullerenes Applicable to Large-Scale Production", Carbon 42, 163 (2004).
C. Thilgen, F. Diederich, R. L. Whetten, "The Higher Fullerenes", Buckminsterfullerenes, Chapter 3, 59 (1993), VCH Publishers, Inc.
I. Bucsi, R. Aniszfeld, T. Shamma, G. K. S. Prakash, G. A. Olah, "Convenient Separation of High-Purity C60 from Crude Fullerenes Extract by Selective Complexation with AlCl3", Proc. Natl. Acad. Sci. U.S.A., 91, 9019 (1994).
T. Anderson, K. Nilsson, M. Sundahl, G. Westman, O. Wennerström, "C60 Embedded in y-Cyclodextrin: a Water-soluble Fullerenes", J. Chem. Soc. Chem. Commun., 604 (1992).
T. Suzuki, K. Nakashima, S. Shinkai, "Very Convenient and Efficient Purification Method for Fullerene (C60) with 5, 11, 17, 23, 29, 35, 41, 47-Octa-tert-butylcalix[8]arene-49, 50, 51, 52, 53, 54, 55, 56-octol", Chem. Lett., 699 (1994).

J. L. Atwood, G. A. Koutsantonis, C. IL. Raston, "Purification of C60 and C70 by Selective Complexation with Calixarenes", Nature 368, 229 (1994).
N. Komatsu, "Preferential Precipitation of C70 over C60 with p-halohomooxa-calix[3]arenes", Org. Biomol. Chem., 204 (2003).
Diederich, F.; Ettl, R.; Rubin, Y.; Wetthen, R. L.; Beck, R.; Alvarez, M.; Anz, S.; Sensharma, D.; Wuld, F.; Khemani, K. C.; Koch A, "The Higher Fullerenes: Isolation and Characterization of C76, C84, C90, C94, and C700, an Oxide of D5h-C7O", Science, 1991, 252, 548-551.
Ettl, E.; Diederich, F; Whetten R.L , "Isolation of C76, a Chiral (D2) Allotrope of Carbon", Nature 1991, 353, 149-153.
Diederich, F; Thilgen, C.; Whetten, R.L; Ettl, E.; Chao, I.; Alvarez, "Fullerene Isomerism: Isolation of C2v-C78 and D3-C78", M.M Science 1991, 254, 1768-1770.
Dennis, T. J. S.; Kai, T.; Tomiyama, T.; Shinohara H., "Isolation and Characterization of the Two Major Isomers of [84] Fullerene (C84)", Chem. Commun 1998, 619-620.
Haino, T.; Fukunaga, C.; Fukazawa Y, "A new Calix[5]arene-Based Container: Selective Extraction of Higher Fullerenes", Org. Lett. 2006, 8, 16, 3545-3548.
Shoji, Y.; Tashiro, K.; Aida, T., "Selective Extraction of Higher Fullerenes Using Cyclic Dimers of Zinc Porphyrins", J. Am. Chem. Soc. 2004, 126, 6570-6571.
Krätschmer, W.; Lamb, L. D.; Fostiropoulos, K.; Huffman D.R., "Solid C60: A New Form of Carbon", Nature 1990, 347, 354.
Hawkins, J. M.; Nambu, M.; Meyer A., "Resolution and Configurational Stability of the Chiral Fullerenes C76, C78 and C84: A Limit for the Activation Energy of the Stone-Wales Transformation", J. Am. Chem. Soc. 1994, 116, 7642.
Crassous, J.; Rivera, J.; Fender, N. S.; Shu, L. H.; Echegoyen, L; Thilgen, C.; Herrmann, A.; Diederich, F. "Chemistry of C84: Separation of Three Constitutional Isomers and Optical Resolution of D2-C84 by Using the Bingel-Retro-Bingel Strategy", Angew., Chem. Int. Ed. 1999, 38, 1613.

(Continued)

*Primary Examiner*—Edward M Johnson
(74) *Attorney, Agent, or Firm*—Peter B. Scull; Kristina M. Kalan; Berenbaum Weinshienk PC

(57) ABSTRACT

A compound of formula I

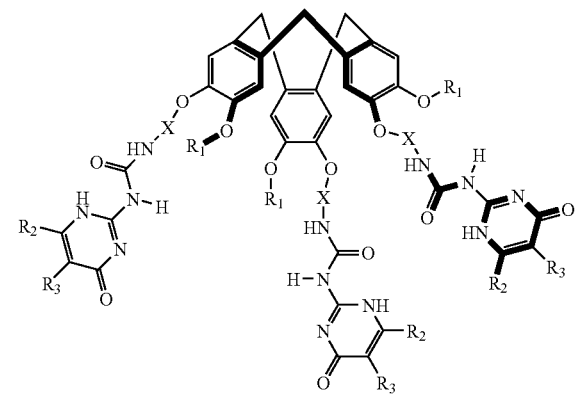

and a corresponding method for the extraction of high-order fullerenes from a carbonaceous mixture including at least one solid-liquid extraction.

17 Claims, 6 Drawing Sheets

OTHER PUBLICATIONS

Wang, G. W.; Saunders, M.; Khong, A.; Cross, R. J., "A New Method for Separating the Isomeric C84 Fullerenes", J. Am. Chem. Soc. 2000, 122, 3216.

Nuffer, R.; Bartl, A.; Dunsch, L.; Mathis C., "Polystyrene Hexa-Adducts of Higher Fullerenes", Synth. Met. 2001, 121, 1151.

Wakahara, T.; Han, A. H.; Niino, Y.; Maeda, Y.; Akasaka, T.; Suzuki, T.; Yamamoto, K.; Kako, M.; Nakadaira, Y.; Kobayashi, K.; Nagase S., "Silylation of Higher Fullerenes", J. Mater. Chem. 2002, 12, 2061.

Darwish, A. D.; Martsinovich, N.; Taylor R., "Methylation of [76] Fullerene and [84] Fullerenes; the First Oxahomo Derivatives of a Higher Fullerene", Org. Biomol. Chem. 2004, 2, 1364.

Shibata, K.; Kubozono, Y.; Kanbara, T.; Hosokawa, T.; Fujiwara, A.; Ito, Y.; Shinohara H., "Fabrication and Characteristics of C84 Fullerene Field-Effect Transistors", Appl. Phys. Lett. 2004, 84, 14, 2572.

Kooistra, F. B.; Mihailetchi, V. D.; Popescu, L. M.; Kronholm, D.; Blom, P. W. M.; Hummelen J. C., "New C84 Derivative and its Application in a Bulk Heterojunction Solar Cell", Chem. Mater. 2006, 18, 3068.

Anthopoulos, D.; Kooistra, F. B.; Wondergem, H. J.; Kronholm, D.; Hummelen, J. C.; de Leeuw D. M., "Air-Stable n-Channel Organic Transistors Based on a Soluble C84 Fullerene Derivative", Adv. Mater. 2006, 18, 1679.

J. W. Steed, P. C. Junk, J. L. Atwood, "Ball and Socket Nanostructures: New Supramolecular Chemistry Based on Cyclotriveratrylene", J. Am. Chem. Soc. 116, 10346 (1994).

H. Matsubara et al., "Supramolecular Inclusion Complexes of Fullerenes Using Cyclotriveratrylene Derivatives with Aromatic Pendants", Chem. Lett., 923 (1998).

H. Matsubara, S.-Y. Oguri, K. Asano, K. Yamamoto, "Syntheses of Novel Cyclotriveratrylenophane Capsules and their Supramolecular Complexes of Fullerenes", Chem. Lett., 431 (1999).

R. P. Sijbesma et al., "Reversible Polymers Formed from Self-Complementary Monomers Using Quadruple Hydrogen Bonding", Science 278, 1601 (1997).

H. M. Keizer et al. "Self-Assembled Pentamers and Hexamers Linked through Quadruple-Hydrogen-Bonded 2-Ureido-4[1H]-Pyrimidinones", Chem. Eur. J. 11, 4602 (2005).

Greene, T.W., Wuts, P.G.M. "Protective Groups in Organic Synthesis", ed. John Wiley and sons, 1999, 3rd edition.

H. M. Keizer et al., The Convenient Synthesis of Hydrogen-Bonded Ureidopyrimidinones'', Eur. J. Org. Chem. 2553 (2004).

Billups, Edward E et al., "Buckminsterfullerenes", 1993 VCH Publishers, Inc., (Chapter 3, inter alia).

A. Hirsch, M. Brettreich, Fullerenes, Chemistry and Reactions, "Fullerenes: Molecular Allotropes of Carbon", Wiley-VCH, Weinheim (2005).

K. C. Khemani, M. Prato, F. Wudl, J. Org. Chem, "A Simple Soxhlet Chromatographic Method for the Isolation of Pure C60 and C70", 57, 3254-3256 (1992).

Greene, T.W., Wuts, P.G.M., "Chapter 2: Protection for the Hydroxyl Group, Including 1,2- and 1,3-Diols", Protective Groups in Organic Synthesis, Third Edition, 1999.

COMPOUND AND METHOD FOR THE SELECTIVE EXTRACTION OF HIGHER FULLERENES FROM MIXTURES OF FULLERENES

This application claims the benefit of U.S. Provisional Application No. 60/833,069; filed Jul. 25, 2006, which is incorporated by reference herein for all that it teaches and discloses.

FIELD

The present disclosure refers to the extraction of fullerenes from carbonaceous mixtures. More specifically, the present disclosure is directed to a novel extracting agent selective for higher-order fullerenes and the corresponding extracting method.

BACKGROUND ART

Progress in the chemistry of higher fullerenes ($>C_{70}$) suffers from the limited availability of these molecular allotropes of carbon, and even the amount of $C_{60}$ (the first most abundant fullerene) and $C_{70}$ (the second most abundant fullerene) produced by sooting flames is less than 9% of the soot mass (see A. Hirsch, M. Brettreich, *Fullerenes, Chemistry and Reactions* (Wiley-VCH, Weinheim, 2005).

Soxhlet-based solid-liquid extractions using toluene, evaporations and tedious chromatographic separations requiring large amounts of solvents are usually employed for the separation and purification of $C_{60}$-$C_{70}$ mixtures (see (a) D. H. Parker et al., *Carbon* 30, 1167 (1992); K. C. Khemani, M. Prato, F. Wudl, *J. Org. Chem.* 57, 3254 (1992); (b) W. A. Scrivens, P. V. Bedworth, J. M. Tour, *J. Am. Chem. Soc.* 114, 7917 (1992); (c) I. L. Isaacs, A. Wehrsig, F. Diederich, *Helv. Chim. Acta* 76, 1231 (1993); (d) N. Komatsu, T. Ohe, K. Matsushige, *Carbon* 42, 163 (2004)). For example, a complete protocol for fullerenes separation by column chromatography and HPLC has been reported by Diederich (C. Thilgen, F. Diederich, R. L. Whetten, *Buckminsterfullerenes*, 59 (1993)).

On the other hand, some separation methods based on selective complexation with Lewis acids have also been described in the background art (I. Bucsi, R. Aniszfeld, T. Shamma, G. K. S. Prakash, G. A. Olah, *Proc. Natl. Acad. Sci. U.S.A.*, 91, 9019 (1994)) or host-guest chemistry, such as encapsulation into cyclodextrins (T. Anderson, K. Nilsson, M. Sundahl, G. Westman, O. Wennerström, *J. Chem. Soc. Chem. Commun.*, 604 (1992)) or calix[8]arenes ((a) T. Suzuki, K. Nakashima, S. Shinkai, *Chem. Lett.*, 699 (1994); (b) J. L. Atwood, G. A. Koutsantonis, C. IL. Raston, *Nature* 368, 229 (1994)). However, apart from their inherent elegance and esthetical appeal, these methods are unpractical because they are selective for the major component $C_{60}$ but not for $C_{70}$ or the higher fullerenes. Komatsu has reported a case of preferential precipitation of $C_{70}$ over $C_{60}$ with p-halohomooxacalix[3]arenes (N. Komatsu, *Org. Biomol. Chem.*, 204 (2003)). Nevertheless, the release of the fullerene and simultaneous recovery of the valuable host from the complex proved difficult, due to its high stability.

Since the discovery of the high order fullerenes, ((a) Diederich, F.; Ettl, R.; Rubin, Y.; Wetthen, R. L.; Beck, R.; Álvarez, M.; Anz, S.; Sensharma, D.; Wuld, F.; Khemani, K. C.; Koch, A. *Science*, 1991, 252, 548-551.; (b) Ettl, E.; Diederich, F; Whetten, R. L *Nature* 1991, 353, 149-153.; (c) Diederich, F; Thilgen, C.; Whetten, R. L; Ettl, E.; Chao, I.; Alvarez, M. M *Science* 1991, 254, 1768-1770.; (d) Dennis, T. J. S.; Kai, T.; Tomiyama, T.; Shinohara, H. *Chem. Commun* 1998, 619-620), the isolation of said compounds is a challenging topic due to their low abundance, poor solubility and difficult separation. Until now, the most reliable method to purify high order fullerenes is HPLC. To reach sufficient purity, however, several cycles are required. The above mentioned drawbacks make the high order fullerenes very expensive. Therefore, high order fullerene chemistry has been poorly developed.

Other methods for the separation of high order fullerenes, based also on supramolecular interactions, have been recently described. For example, a new double calix[5]arene container successfully extracts higher fullerenes, especially $C_{94}$ and $C_{96}$, from fullerene mixtures. The syn-isomer of the double calix[5]arene selectively captures higher fullerenes from fullerene mixtures (Haino, T.; Fukunaga, C.; Fukazawa, Y. *Org. Lett.* 2006, 8, 3545-3548). By raising the temperature above 100° C., a conformational change to the anti isomer is promoted, thus releasing the captured high order fullerenes.

Other methods based on host-guest chemistry have been described, for example, Aida's cyclic dimers of zinc porphyrins (Shoji, Y.; Tashiro, K.; Aida, T. *J. Am. Chem. Soc.* 2004, 126, 6570-6571). These compounds are useful for the extraction of fullerenes $\geq C_{76}$ directly from fullerene mixtures, and upon several extractions, allow the enrichment of rare fullerenes $C_{102}$-$C_{110}$.

All the above described host-guest methods are beautifully designed but in all cases, chromatography is required in some step of the process.

The higher fullerene $C_{84}$ is the third most abundant fullerene after $C_{60}$ and $C_{70}$ and has a total of 24 isomers (see a) Krätschmer, W.; Lamb, L. D.; Fostiropoulos, K.; Huffman, D. R. Nature 1990, 347, 354. b) Diederich, F.; Ettl, R.; Rubin, Y.; Whetten, R. L.; Beck, R.; Alvarez, M.; Anz, S.; Sensharma, D.; Wudl, F.; Khemani, K. C.; Koch, A. Science 1991, 252, 548). As a result of the very limited availability of pure $C_{84}$ only very few reactions have been carried out on this fullerene and most of them have been performed on a very small scale with the goal to separate the different isomers or to test the reactivity of $C_{84}$ (see a) Hawkins, J. M.; Nambu, M.; Meyer, A. J. Am. Chem. Soc. 1994, 116, 7642. b) Crassous, J.; Rivera, J.; Fender, N. S.; Shu, L. H.; Echegoyen, L.; Thilgen, C.; Herrmann, A.; Diederich, F. Angew. Chem. Int. Ed. 1999, 38, 1613. c) Wang, G. W.; Saunders, M.; Khong, A.; Cross, R J. J. Am. Chem. Soc. 2000, 122, 3216. d) Nuffer, R.; Bartl, A.; Dunsch, L.; Mathis, C. Synth. Met. 2001, 121, 1151. e) Wakahara, T.; Han, A. H.; Niino, Y.; Maeda, Y.; Akasaka, T.; Suzuki, T.; Yamamoto, K.; Kako, M.; Nakadaira, Y.; Kobayashi, K.; Nagase, S. J. Mater. Chem. 2002, 12, 2061. f) Darwish, A. D.; Martsinovich, N.; Taylor, R. Org. Biomol. Chem. 2004, 2, 1364). $C_{84}$ has potential applications in the fields of nonlinear optics and superconductivity (see Shibata, K.; Kubozono, Y.; Kanbara, T.; Hosokawa, T.; Fujiwara, A.; Ito, Y.; Shinohara, H. Appl. Phys. Lett. 2004, 84, 2572) and can be used to develop organic solar cell devices ((a) Kooistra, F. B.; Mihailetchi, V. D.; Popescu, L. M.; Kronholm, D.; Blom, P. W. M.; Hummelen, J. C. Chem. Mater. 2006, 18, 3068. b) Anthopoulos, D.; Kooistra, F. B.; Wondergem, H. J.; Kronholm, D.; Hummelen, J. C.; de Leeuw, D. M. Adv. Mater. 2006, 18, 1679) and organic field effect transistors (see Shibata, K.; Kubozono, Y.; Kanbara, T.; Hosokawa, T.; Fujiwara, A.; Ito, Y.; Shinohara, H. Appl. Phys. Lett. 2004, 84, 2572).

SUMMARY

Provided here is a method for the selective extraction of high-order fullerenes which overcomes the deficiencies of the prior art.

This is solved according to a first aspect hereof by providing a compound of general formula:

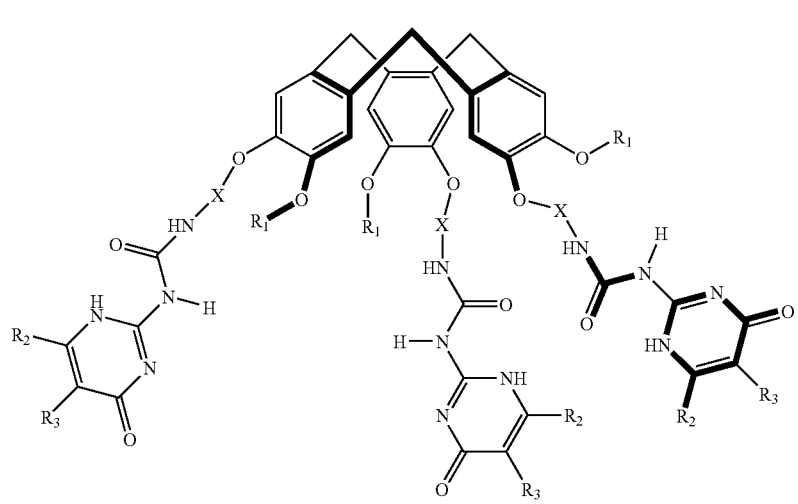

I wherein O—X—NH— is a $C_2$ to $C_5$ alkyl, aryl or benzyl;

$R_1$ is selected from the group comprising linear or branched alkyl and polyethers, optionally unsaturated;

$R_2$ and $R_3$ are selected independently from the group comprising H, hydroxyl, protected alcohol functionalities, ether, acyl, carboxylate, alkoxycarbonyl;

linear or branched alkyl optionally unsaturated and optionally substituted by one or more of the following: carbocycles, heterocarbocycles, aromatic rings, heteroaromatic rings, hydroxyl, protected alcohol functionalities, ether, acyl, carboxylate and akoxycarbonyl;

cycloalkyl, heterocycloalkyl, aryl, heteroaryl, benzyl which are optionally substituted by one or more of the following: alkyl, hydroxyl, protected alcohol functionalities, ether, acyl, carboxylate and alkoxycarbonyl;

or wherein $R_2$ and $R_3$ together form a carbocyclic or heterocyclic group having from 5 to 8 members, optionally fused to other cyclic systems and optionally substituted by one or more of the following: alkyl, hydroxyl, protected alcohol functionalities, ether, acyl, carboxylate and alkoxycarbonyl.

Compounds of formula I comprise a cyclotriveratrilene (referred to as CTV) scaffold and three 2-ureido-4-[1H]-pyrimidinone moieties (referred to as UPy). Atwood et al. have reported the formation of so-called "ball and socket" 1:1 complexes between CTV and $C_{60}$ (J. W. Steed, P. C. Junk, J. L. Atwood, *J. Am. Chem. Soc.* 116, 10346 (1994)). However, 2:1 complexes of CTV with $C_{60}$ have been described only rarely (H. Matsubara et al., *Chem. Lett.,* 923 (1998); H. Matsubara, S.-Y. Oguri, K. Asano, K. Yamamoto, *Chem. Lett.,* 431 (1999)). On the other hand, UPy dimers have been employed frequently as noncovalent bonding subunits to construct supramolecular architectures, such as polymers (R. P. Sijbesma et al., *Science* 278, 1601 (2002)) or oligomeric cyclic aggregates (rosettes) (H. M. Keizer et al., *Chem. Eur. J.* 11, 4602 (2005)), among others.

Surprisingly, the combination of a concave cyclotriveratrilene (CTV) unit capable of complexing fullerenes with the strongly quadruple hydrogen bonding ureidopyrimidinone resulted in a new family of compounds of formula I which form well-defined dimeric hydrogen-bonded assemblies with the capacity of encapsulating a fullerene molecule into its large cavity. Non-covalently linked capsules based on CTV have not been described in the background art. Advantageously, the system displays a remarkable selectivity for the encapsulation of high-order fullerenes over $C_{60}$, thus allowing the separation and extraction of high-order fullerenes from carbonaceous mixtures.

In a preferred implementation, compound I is of formula Ia:

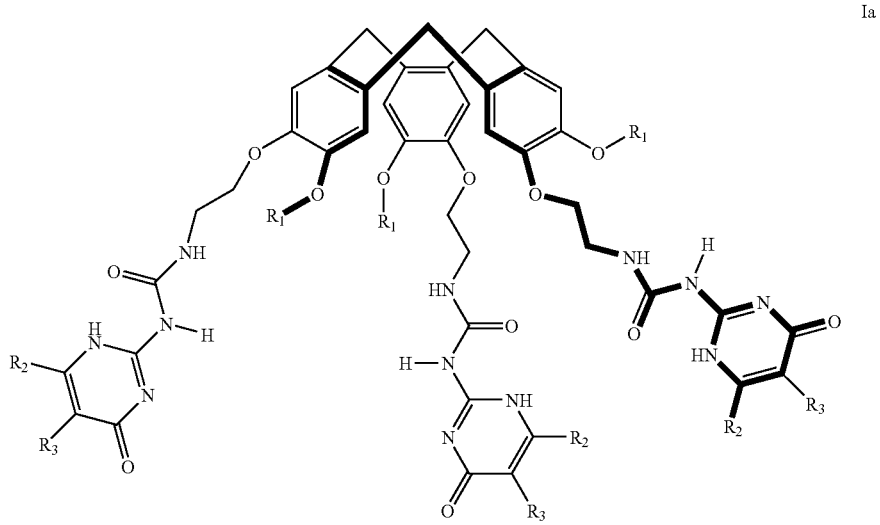

wherein $R_1$ is selected from the group comprising linear or branched alkyl and polyethers, optionally unsaturated;

$R_2$ and $R_3$ are selected independently from the group comprising H, hydroxyl, protected alcohol functionalities, ether, acyl, carboxylate, alkoxycarbonyl;

linear or branched alkyl optionally unsaturated and optionally substituted by one or more of the following: carbocycles, heterocarbocycles, aromatic rings, heteroaromatic rings, hydroxyl, protected alcohol functionalities, ether, acyl, carboxylate and akoxycarbonyl;

cycloalkyl, heterocycloalkyl, aryl, heteroaryl, benzyl which are optionally substituted by one or more of the following: alkyl, hydroxyl, protected alcohol functionalities, ether, acyl, carboxylate and alkoxycarbonyl;

or wherein $R_2$ and $R_3$ together form a carbocyclic or heterocyclic group having from 5 to 8 members, optionally fused to other cyclic systems and optionally substituted by one or more of the following: alkyl, hydroxyl, protected alcohol functionalities, ether, acyl, carboxylate and alkoxycarbonyl.

Alternatively, in another implementation, a compound of formula I is provided wherein:

O—X—NH— is selected from the group comprising:

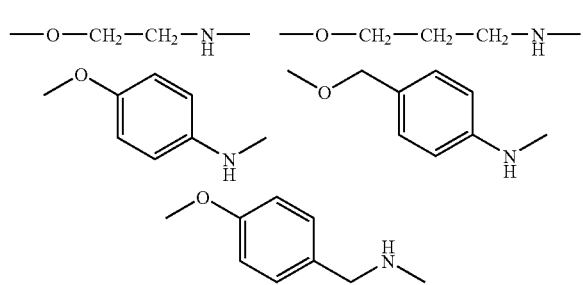

$R_1$ is selected from the group comprising linear or branched alkyl and polyethers, optionally unsaturated.

$R_2$ and $R_3$ are selected independently from the group comprising H, hydroxyl, protected alcohol functionalities, ether, acyl, carboxylate, alkoxycarbonyl;

linear or branched alkyl optionally unsaturated and optionally substituted by one or more of the following: hydroxyl, protected alcohol functionalities, ether, acyl, carboxylate, alkoxycarbonyl, esters and derivatives;

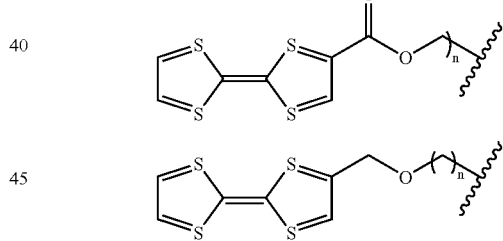

wherein n is an integer from 2 to 4

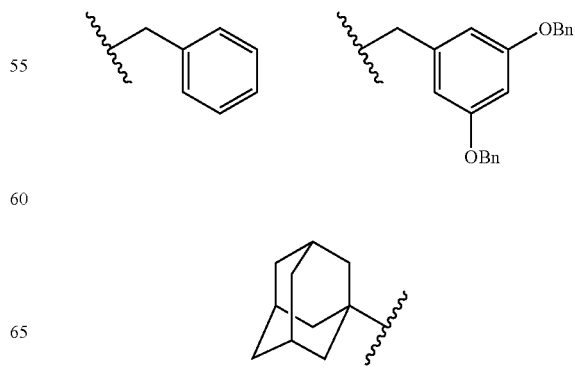

-continued

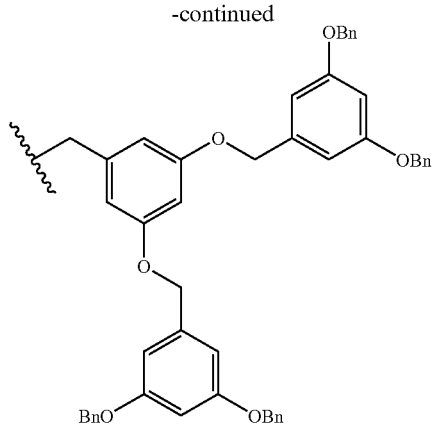

or wherein $R_2$ and $R_3$ together form

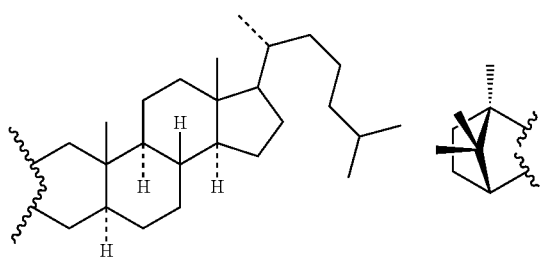

In a further implementation, compound I is of formula 1:

According to a second aspect, the present disclosure provides a fullerene-extracting composition including a compound of general formula I.

In a third aspect, the present disclosure refers to a capsule including two units of a compound of formula I non-covalently linked.

According to a fourth aspect, the present disclosure provides a non-covalently linked complex including a high-order fullerene and two units of a compound of general formula I. For example, said complex comprises $C_{70}$ and two units of a compound of general formula I.

In a fifth aspect, the present disclosure relates to a method for the preparation of a compound of formula Ia according hereto including the following operations:

(a) reacting a CTV-compound of formula IIIa with $NaN_3$ to form the corresponding azide derivative IVa;

(b) treating the CTV-azide derivative IVa obtained in operation a with triphenylphosphine and ammonia to form a CTV-derivative of formula Va;

(c) reacting the CTV-derivative of formula Va with an imidazolide of formula IIa (see Scheme 1 below).

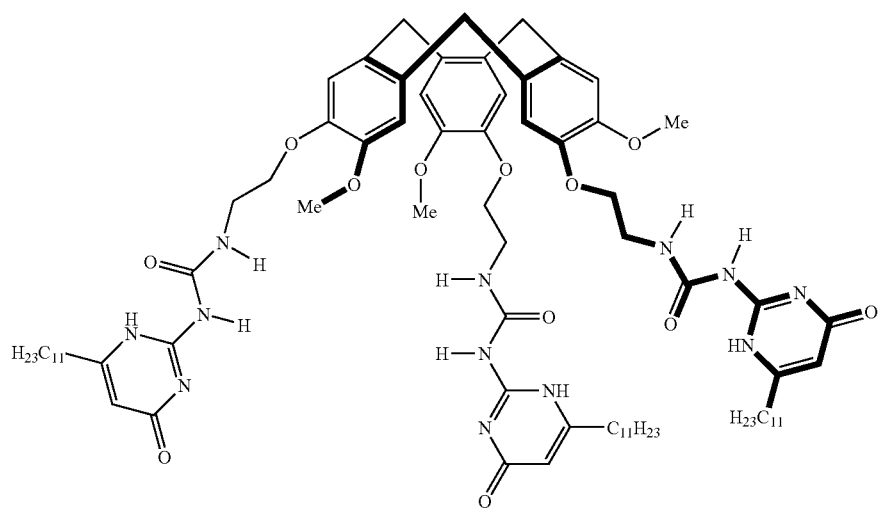

1

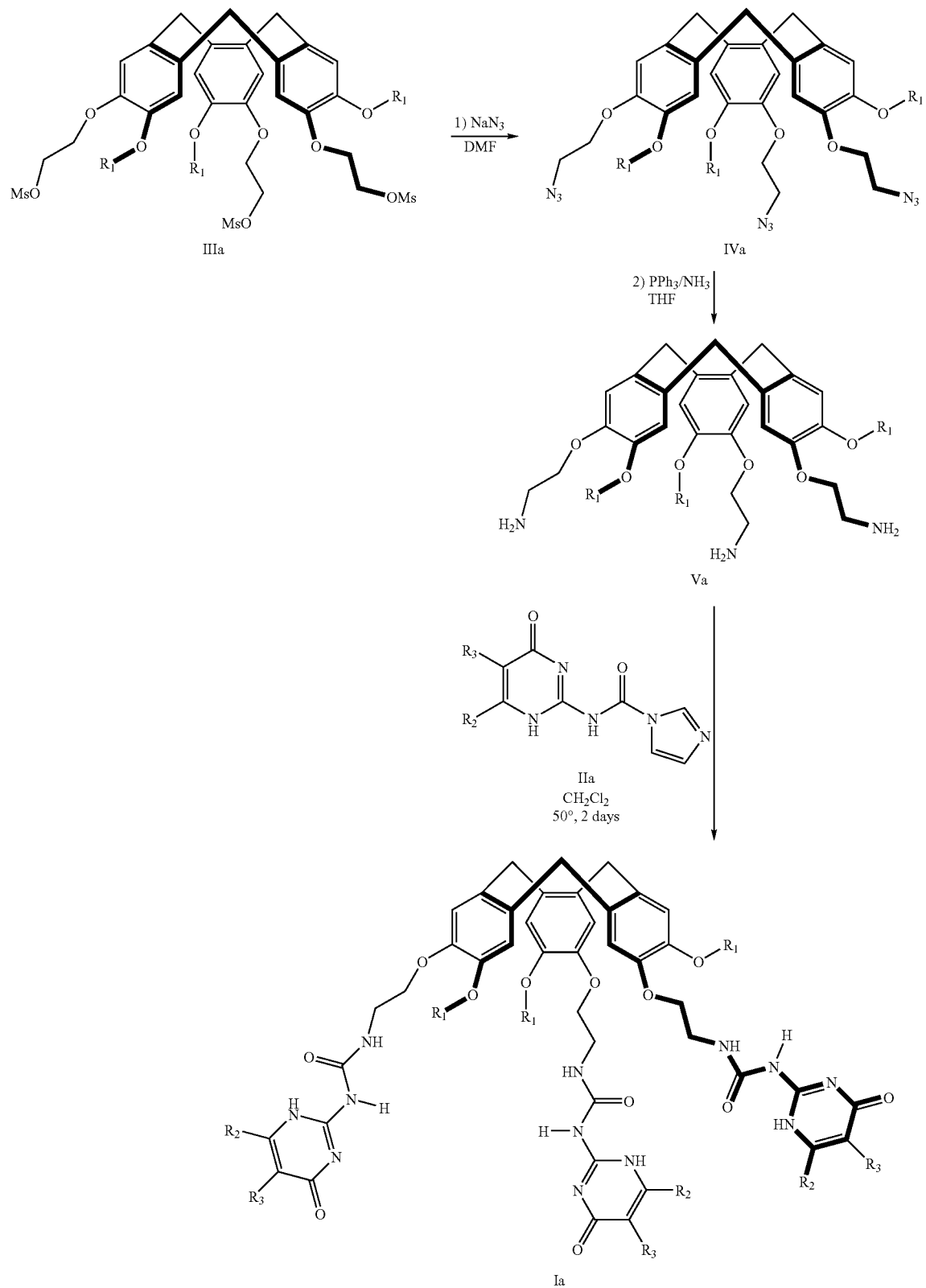
Scheme 1

Advantageously, the preparation method hereof is straightforward; it is performed at mild conditions and can be easily scaled-up. More advantageously, high yields are obtained by the preparation method hereof and no further purification step being necessary.

According to a sixth aspect, the present disclosure provides a method for the extraction of high-order fullerenes from a carbonaceous mixture characterized in that it includes at least one solid-liquid extraction by using a compound of formula I as extracting agent and a polar aprotic solvent or mixture of solvents as solvent.

More specifically, the present disclosure provides a method for the extraction of high-order fullerenes from a carbonaceous mixture including the following operations:
(a) contacting the carbonaceous mixture in a polar aprotic solvent or mixture of solvents with a compound of formula I and stirring;
(b) separating the liquid from the solid;
(c) adding at least one disrupting compound selected from the group including polar solvents and acids to the liquid;
(d) isolating the precipitated high-order fullerenes.

Advantageously, the method for the extraction of high-order fullerenes according hereto is based on simple solid-liquid extractions, no chromatographic separation being necessary.

Advantageously, dimers of compounds of general formula I and the complexes between compounds of general formula I and high-order fullerenes are soluble in polar aprotic solvents or mixtures of solvents, in contrast to non-complexed fullerenes which are highly insoluble in them, thus allowing the extraction of high-order fullerenes from carbonaceous mixtures, in particular from carbonaceous mixtures comprising $C_{60}$, simply by solid-liquid extraction.

A further advantage of the method for the extraction of high-order fullerenes according hereto is that the host-guest complex having two units of a compound of general formula I and a fullerene easily dissociates into smaller, non-complexed fragments upon addition of polar solvents or under the influence of acids, thus allowing the recovery of the corresponding fullerene. Advantageously, the compound of formula I can be isolated, for example by evaporation, and recycled. The possibility of recycling the extracting agent makes the method for the extraction of high-order fullerenes according hereto very suitable for industrial applications.

The fullerene fraction obtained by the method hereof can be subjected to further rounds of solid-liquid extractions according to the method hereof until obtaining the desired purity of the extracted high-order fullerene. An ordinary-skilled person in the art will understand that the purity of the fullerenes obtained will increase as increasing the number of solid-liquid extraction rounds. Preferably, from one to four rounds of solid-liquid extractions are performed.

In a preferred implementation of the extraction method hereof, the polar aprotic solvent or mixture of solvents is tetrahydrofurane (THF) or acetonitrile (MeCN). In a further implementation hereof, the disrupting compound is an acid, for example trifluoroacetic acid (TFA).

Preferably, the amount of compound of formula I employed according to the extraction method hereof is from about 5% to about 60% (w/w) relative to the carbonaceous mixture.

A further advantage of the extraction method according hereto is that it allows the isolation of high-order fullerenes, which can not be readily isolated by using the methods of the background art. For example, even by using a short number of solid-liquid extraction rounds, the fullerene[70] extracted by the method hereof can be obtained with high purity, preferably with a purity higher than 80%, more preferably with a purity higher than 90%, even more preferably with a purity higher than 95%. Alternatively, fullerenes higher than $C_{70}$ can be extracted by the method hereof.

In a preferred implementation of the extraction method hereof, $C_{70}$ is obtained. Advantageously, the possibility of isolating $C_{70}$ opens the way to further investigation of the properties and applications of these $C_{70}$ fullerenes in industry.

In another implementation $C_{84}$ is obtained. Preferably, according to this implementation, a compound of formula I wherein X is a $C_2$ alkyl is employed. Surprisingly, the method hereof allows isolating $C_{84}$ from carbonaceous mixtures. Advantageously, the possibility of isolating $C_{84}$ opens the way to further investigation of the properties and applications of these $C_{84}$ fullerenes in industry.

Alternatively, other high-order fullerenes from $C_{70}$ to $C_{96}$ can be obtained by the method hereof. Advantageously, the possibility of isolating high order fullerenes according to the method hereof opens the way to an easy and practical access to these materials, which can not be effectively isolated by using the methods of the background art. The selection of the length of X in formula I has an influence on the size of the capsule. Longer X chains will give rise to larger capsules which could encapsulate larger guests and therefore, longer X chains will be more suitable for encapsulating higher order fullerenes. The selection of the most suitable X chain of an extracting agent of formula I in order to make it more selective for a particular high order fullerene can be determined by experimentation and is within the skill in the art. For example, for the isolation of $C_{70}$ according to the method hereof, shorter X chains in the extracting compounds of formula I are selected, for example a $C_2$ alkyl. On the other hand, the weight ratio of the extracting agent to the carbonaceous mixture has also an influence on the selectivity for a given fullerene. The most suitable weight ratio of the extracting agent to the fullerenes mixture can be determined by experimentation and is within the skill in the art.

In a seventh aspect, the present disclosure refers to the use of a compound of formula I as a fullerene-extracting agent.

Prior to a discussion of the detailed implementations of the process according hereto, a definition of specific terms related to the main aspects hereof is provided.

A "high-order fullerene" as defined in the present disclosure refers to a fullerene containing more than 60 carbon atoms.

A "carbonaceous mixture" as defined in the present disclosure refers to a mixture including fullerenes and optionally including carbon containing materials.

The term "soot" as defined in the present disclosure refers to the product produced by sooting flames on graphite, typically including about 7-9% fullerenes and carbonaceous tar of unknown composition.

The term "fullerite" as defined in the present disclosure refers to the fullerene mixture arising from extraction of soot with toluene, typically including $C_{60}$ (70-90%), $C_{70}$ (10-30%) and higher fullerenes (less than 2%).

The term "protected alcohol functionalities" refers to an alcohol protected according to methods known to an ordinary-skilled person in the art. See for example Greene, T. W., Wuts, P. G. M. "Protective Groups in Organic Synthesis", ed. John Wiley and sons, 1999, $3^{rd}$ edition.

Additional aspects, advantages and features hereof will become apparent to those skilled in the art upon examination of the description or may be learned by practice of the subject matter of this disclosure. The following examples and drawings are provided by way of illustration and are not intended to limit the scope of the disclosure. It is intended that the scope hereof be defined by the claims appended hereto.

DETAILED DESCRIPTION OF PARTICULAR EXAMPLES

Example 1

Preparation of the Extracting Agent (1)

Figure 1:
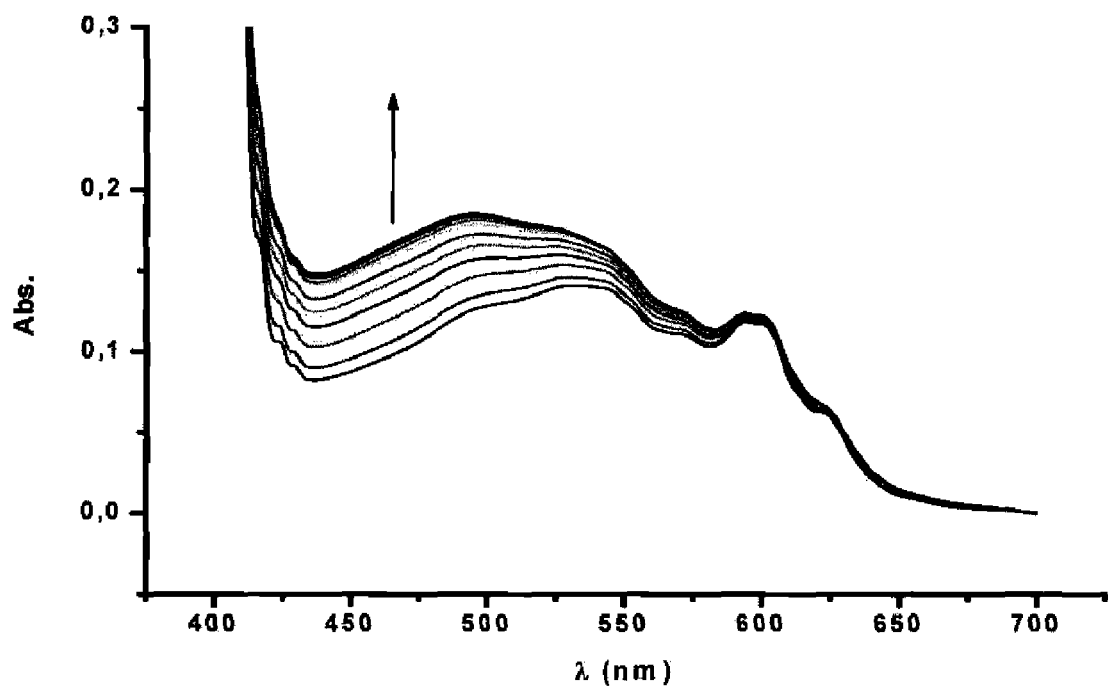
FIG. 1 shows the UV-titration of extracting agent 1 with $C_{60}$, according to Example 2.

1.a Preparation of N-(1,4-dihydro-4-oxo-6-undecylpyrimidin-2-yl)-1H-imidazole-1-carboxamide (2)

Compound 2 can be prepared according to methods described in the background art, for example by the method described by H. M. Keizer et al. *Eur. J. Org. Chem.* 2553 (2004).

Characterization of Compound 2:

Mp 179° C.

$^1$H-NMR (CDCl$_3$, 400 MHz): δ 8.88 (s, 1H, NCHN), 7.67 (s, 1H, NCHCH), 7.04 (s, 1H, NCHCH), 5.83 (s, 1H, OCCHC), 2.67 (t, J=7.6 Hz, 2H, HNCH$_2$CH$_2$), 1.78 (q, J=7.6 Hz, 2H, HNCH$_2$CH$_2$), 1.51-1.21 (m, 16H, CH$_2$), 0.90 [t, J=7.7 Hz, 3H, (CH$_2$)$_{10}$CH$_3$].

$^{13}$C-NMR (DMSO-d$_6$, 125 MHz): δ 161.0 (C), 157.2 (C), 156.7 (C), 135.0 (CH), 122.0 (CH), 117.6 (CH), 103.5 (CH), 32.9 (CH$_2$), 31.9 (CH$_2$), 29.6 (CH$_2$), 29.4 (CH$_2$), 29.3 (CH$_2$), 29.2 (CH$_2$), 29.0 (CH$_2$), 27.5 (CH$_2$), 22.7 (CH$_2$), 14.1 (CH$_3$).

HRMS calcd for C$_{16}$H$_{26}$N$_3$O$_2$ [(M$^+$H-imidazole)$^+$]: 292.2025. Found: 292.2025.

Anal. Calcd. for C$_{19}$H$_{29}$N$_5$O$_2$ (359.2): C, 63.48; H, 8.13; N, 19.48. Found: C, 63.51; H, 8.14; N, 19.43.

1.b Preparation of (±)-2,7,12-Tris(2-aminoethoxy)-3,8,13-trimethoxy-10,15-dihydro-5H-tribenzo[a,d,g]cyclononene (5)

Compound 5 was synthesized from compound 3 according to scheme 2. Trimesylate 3 (1.2 g, 1.55 mmol) was dissolved in DMF (10 mL) and NaN$_3$ (2 g, 30 mmol) was added. The suspension was stirred overnight at 50° C. The mixture was poured into 400 mL ice-water, the off-white precipitate was filtered and washed several times with cold water. The still wet azide intermediate 4 was then treated with triphenylphosphine (2.46 g, 9.3 mmol) in THF (50 mL) for 2 h. Concentrated ammonia (1 mL) was added and the solution was stirred overnight at room temperature. The solvent was evaporated and the product was precipitated by addition of Et$_2$O (500 mL), filtered off and thoroughly washed with Et$_2$O. Recrystallization from hot methanol afforded pure triamine 5 (0.74 g, 89%) as a white solid.

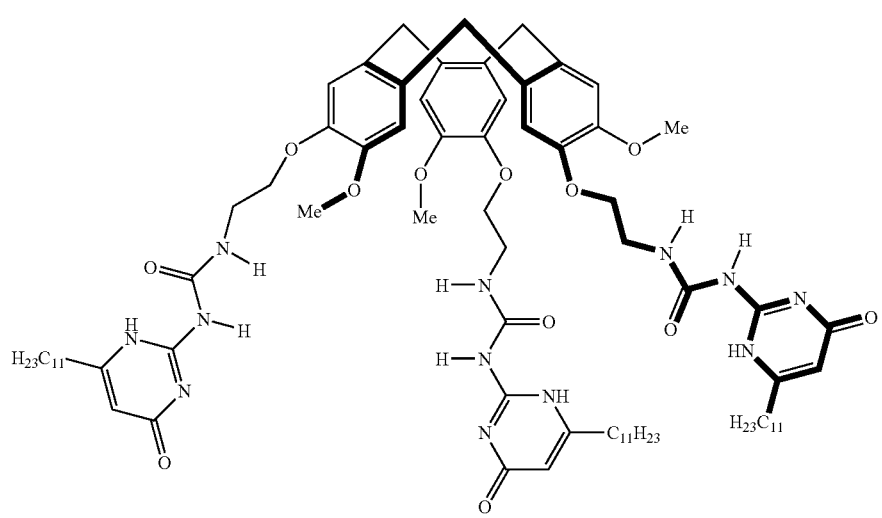

Compound 1

Scheme 2

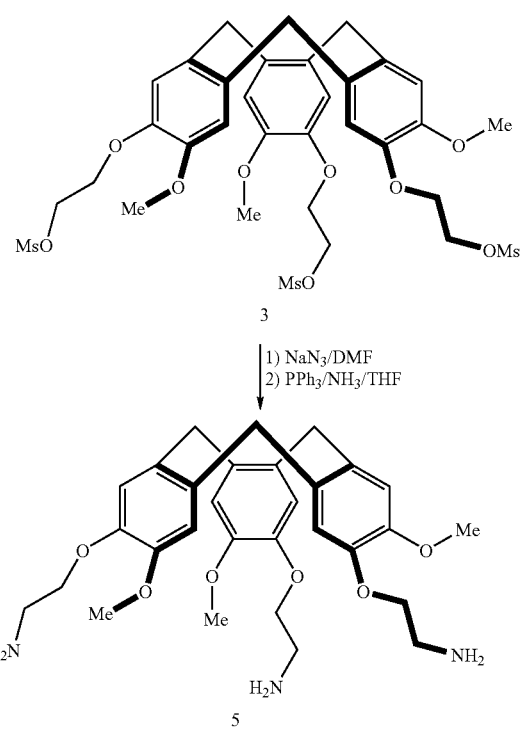

Characterization of Compound 5:

$^{1}$H-NMR (CD$_3$OD, 300 MHz): δ 6.92 (s, 3H, Ar), 6.90 (s, 3H, Ar), 4.53 (d, J=13.6 Hz, 3H, ArCH$_2$Ar), 3.91 (m, 6H, OCH$_2$), 3.74 (s, 9H, OCH$_3$), 3.35 (d, J=13.6 Hz, 3H, ArCH$_2$Ar), 2.86 (t, 9H, CH$_2$N).

$^{13}$C-NMR (CD$_3$OD, 75 MHz): δ 147.6 (Ar), 146.3 (Ar), 132.2 (Ar), 131.9 (Ar), 115.3 (Ar), 113.8 (Ar), 71.0 (OCH$_2$), 55.6 (OCH$_3$), 40.7 (CH$_2$N), 34.9 (ArCH$_2$Ar).

FAB-MS: m/z 538.0 [(M$^+$H)]$^+$.

1c. Preparation of (±)-2,7,12-Tris{N-[(aminoethoxy)carbonyl]-6-undecanylisocytosine}-3,8,13-trime-thoxy-10,15-dihydro-5H-tribenzo[a,d,g]cyclononene (1)

Compound 1 was synthesized from compound 2 according to Scheme 3. A suspension of imidazolide 2 (90 mg, 0.25 mmol) and triamino-CTV 5 (40 mg, 0.07 mmol) in 3 mL of CH$_2$Cl$_2$ was stirred at 50° C. in a sealed tube for 2 days. The reaction mixture was subsequently added to 10 mL of methanol under vigorous stirring to result in a white solid. After sonicating the suspension for 1 minute, the solid was allowed to sink to the bottom of the tube. The supernatant was decanted and the remaining solid was washed with methanol after which the methanol was decanted (3×). The resulting white solid was dried under air to yield 1 (92 mg, 88%).

Characterization of Compound 1:

Mp=140-142° C.

1H-NMR (DMSO-d$_6$, 400 MHz) δ 11.48 (s, 3H, NH), 9.79 (s, 3H, NH), 7.66 (s, 3H, NH), 7.13 (s, 3H, Ar), 7.08 (s, 3H, Ar), 5.75 [s, 3H, CHC(O)], 4.68 (d, J=13.2 Hz, 3H, CH$_2$-bridge), 3.50 (d, J=13.2 Hz, 3H, CH$_2$-bridge), 4.03 (m, 6H, OCH$_2$), 3.69 (s, 9H, OCH$_3$), 3.47 (m, 6H, CH$_2$NH), 2.30 (t, J=7.6 Hz, 6H, CCH$_2$-alkyl), 1.51 (m, 6H, CCH$_2$CH$_2$-alkyl), 1.18 (m, 48H, CH$_2$-alkyl), 0.83 (t, J=6.8 Hz, 9H, CH$_2$CH$_3$,).

$^{13}$C-NMR (DMSO-d$_6$, 125 MHz): δ 161.2, 154.6, 151.0, 147.8, 146.1, 132.6, 131.9, 117.1, 116.2, 114.4, 103.5, 78.7, 67.9, 55.8, 35.8, 34.7, 30.7, 28.4, 28.3, 28.2, 28.1, 27.9, 26.7, 21.5, 13.2.

ES-MS+ m/z 1412 [(M+H)+].

Anal. Calcd. For C$_{78}$H$_{114}$N$_{12}$O$_{12}$ (1410.9): C, 66.36; H, 8.14; N, 11.91. Found: C, 66.27; H, 8.47; N, 11.73.

Scheme 3

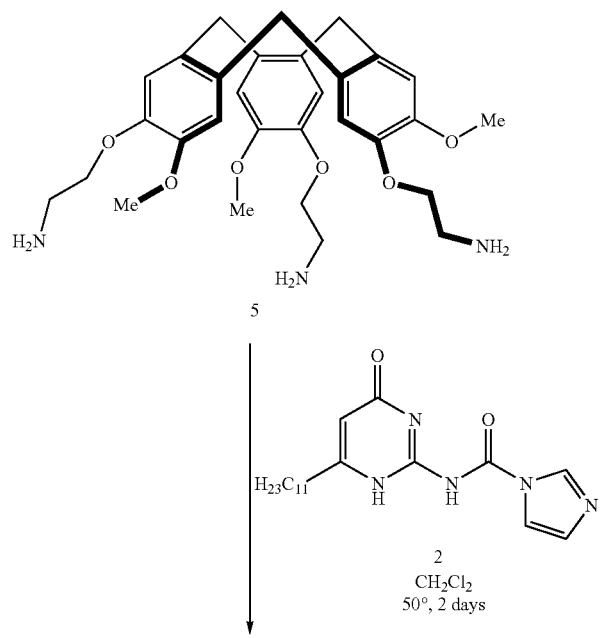

-continued

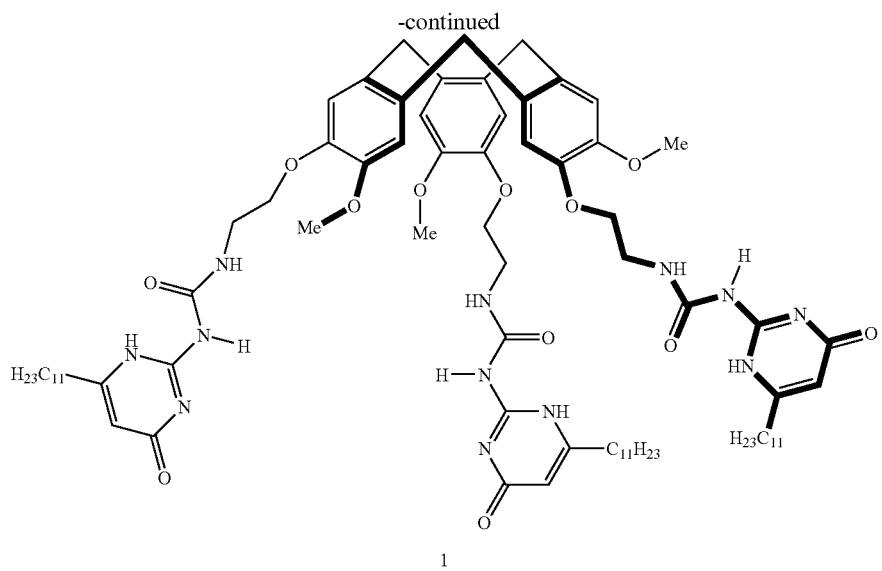

1

Example 2

Extraction of $C_{70}$ from fullerite by using (±)-2,7,12-Tris{N-[(aminoethoxy)carbonyl]-6-undecanylisocyto-sine}-3,8,13-trimethoxy-10,15-dihydro-5H-tribenzo[a,d,g]cyclononene (1) as extractant 2.a Method for the Extraction of $C_{70}$ from Different Mixtures of Fullerenes Different fullerene mixtures were suspended in the appropriate amount of a $1.2 \times 10^{-3}$ M solution of CTV-Upy (THF) and diluted to the same volume with pure THF. The mixtures were stirred over 15 minutes. No sonication or heat was used in the extraction. The mixtures were filtered and samples of 400 μL of solution were diluted in 500 μL of toluene and 10 μL of TFA. Subsequently, the composition of the extracted samples were analyzed by HPLC. The results are summarized in Table 1:

TABLE 1

Fullerene extraction selectivities

| Entry | Initial Ratio [$C_{60}/C_{70}/1_2$] (mol equiv) | Extract Composition (%)* | |
|---|---|---|---|
| | | $C_{70}$ | $C_{60}$ |
| 1 | [1:1:1] | 87.26 | 12.74 |
| 2 | [1:1:0.5] | 96.38 | 3.62 |
| 3 | [1:12:11] | 99.31 | 0.69 |
| 4 | [6:1:1] | 92.47 | 7.53 |

*Inherent solubility of fullerenes in dry THF has been subtracted

The extraction method according to the present disclosure by using compound 1 as extractant proved to be very efficient for the extraction of $C_{70}$ from mixtures of $C_{60}$ and $C_{70}$. By performing just a single solid-liquid extraction, $C_{70}$ was obtained with high purities from 87% to 99%, depending on the composition of the initial fullerene mixture.

2.b Method for the Extraction of $C_{70}$ from Fullerite

A solution of 3.8 mg of 1 in THF (2 mL) was added to 20.9 mg of solid fullerite. The mixture was stirred for 15 minutes at 22° C. and was filtered to eliminate the solid residue. An aliquot was analyzed by HPLC. The first extraction gives an 84:16 $C_{70}/C_{60}$ mixture. The solution was treated with 50 μL of trifluoroacetic acid (TFA) to break the hydrogen bonds between the UPy's. The suspension of precipitated fullerenes was centrifuged (5 min, 4500 rpm), the solvent was removed and the solid residue was redissolved in carbon disulphide ($CS_2$) and the recovered fullerenes dried in vacuum. The solid was re-extracted with 1.60 mg of CTV as described above giving a 97:3 $C_{70}/C_{60}$ mixture.

Figure 2:
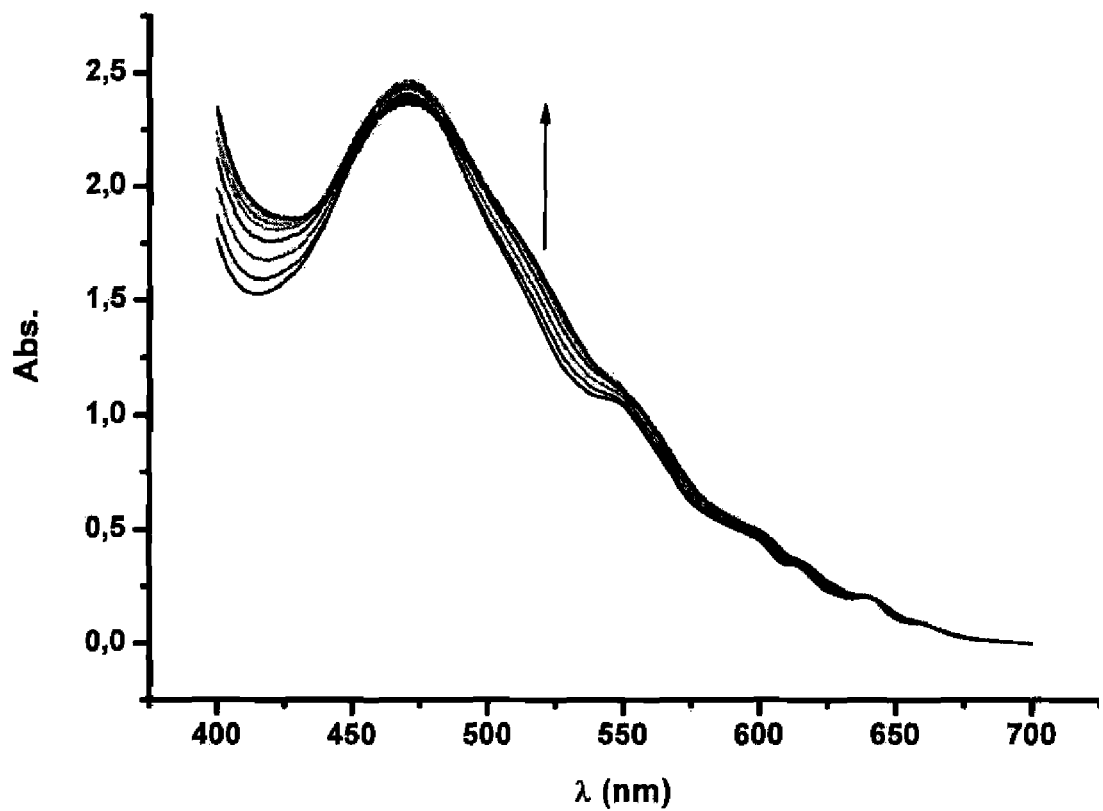
FIG. 2 shows the UV-titration of extracting agent 1 with $C_{70}$, according to Example 2.
Figure 3:
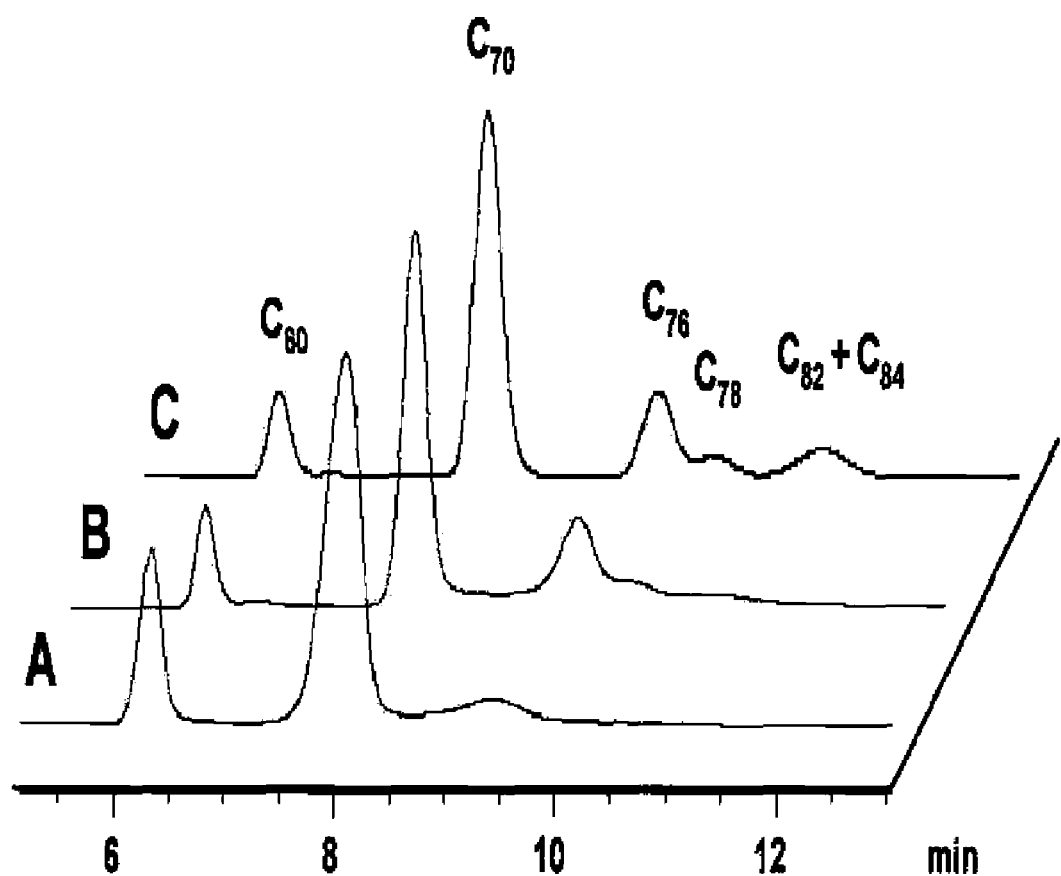
FIG. 3 shows the fullerene ratios upon extraction of fullerite with variable amounts of extracting agent 1, according to Example 2. The percentage by weight of agent 1 relative to fullerite is as follows: (A) 67%; (B) 34%; and (C) 18%.

The corresponding binding studies for $C_{60}$ and $C_{70}$ are shown in FIGS. 1 and 2, respectively. FIG. 3 shows the fullerene ratios upon extraction of fullerite with variable amounts of compound 1.

The method hereof by using compound 1 as the extracting agent allowed extraction of $C_{70}$ from fullerite with high purifies: 85% purity after a single solid-liquid extraction and up to 97% after two solid-liquid extractions. Therefore, the extraction method according hereto allows extracting high-order fullerenes with high purity through simple solid-liquid extractions, avoiding the use of chromatography.

2.c Method for the Extraction of $C_{84}$

Figure 4:
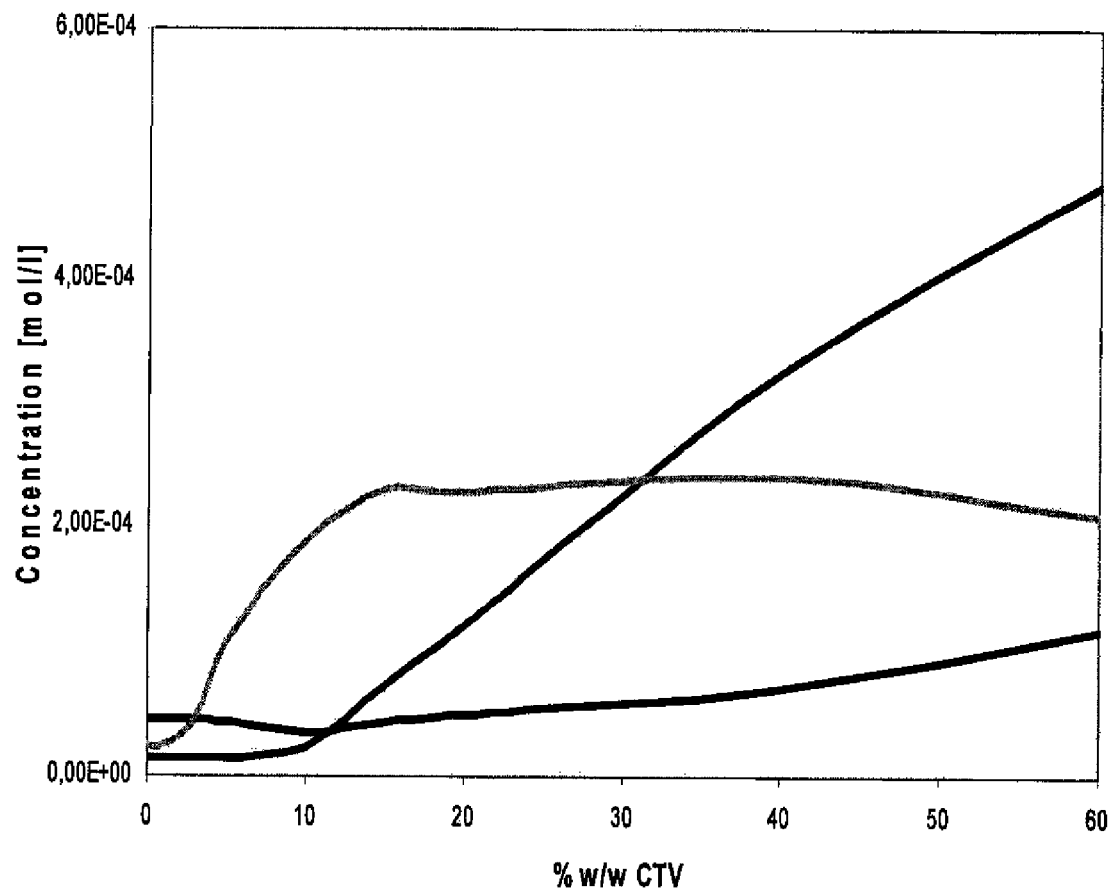
FIG. 4 shows the variation of the concentration of the extracted fullerenes $C_{60}$, $C_{70}$ and $C_{84}$ upon increasing the ratio of extracting agent 1 to fullerite, according to Example 2.c.

As depicted in FIG. 4, $C_{84}$ is extracted preferentially over $C_{60}$ and $C_{70}$ at low concentrations of host.

Thus, a solution of 0.75 mg of compound 1 in THF (2.5 mL) was added to 15.03 mg of solid fullerite. The mixture was stirred for 8 hours at 22° C. and was filtered to eliminate the solid residue. A first solid-liquid extraction yields a $C_{84}$ enriched mixture (18.6% $C_{60}$, 6.1% $C_{70}$ and 75.2% $C_{84}$). The mixture can be enriched in $C_{84}$ up to substantially pure $C_{84}$ through subsequent extractions.

In order to release $C_{84}$ from compound 1, the solution was treated with 50 μL of trifluoroacetic acid (TFA) to break the hydrogen bonds between the UPy's. Solvent was eliminated, the solid residue was redissolved in carbon disulphide, filtered ($CS_2$) and dried in vacuum.

2.d Method for the Extraction of Other High Order Fullerenes

The procedure as depicted in Example 2.c was repeated by using variable weight ratios of extracting agent to fullerite.

Figure 5:
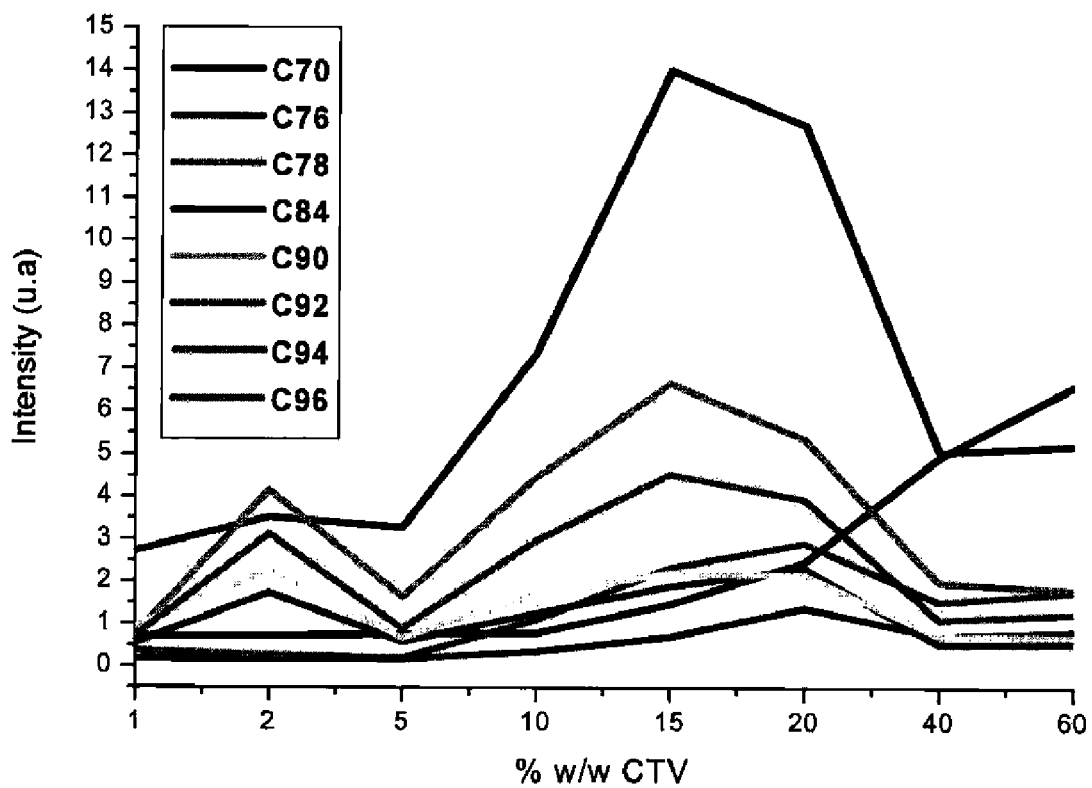
FIG. 5 is a qualitative analysis of the variation of the concentration of the extracted fullerenes by using variable amounts of CTV-UPy (% weight to fullerite) after a single solid-liquid extraction with compound 1, according to Example 2.d. The extractions were analyzed by MALDI-TOF mass spectrometry after 24 h stirring at room temperature. The signals obtained for each fullerene was normalised with respect to the signal of $C_{60}$ and plotted versus the ratio of extracting agent 1 to fullerite used.
Figure 6:
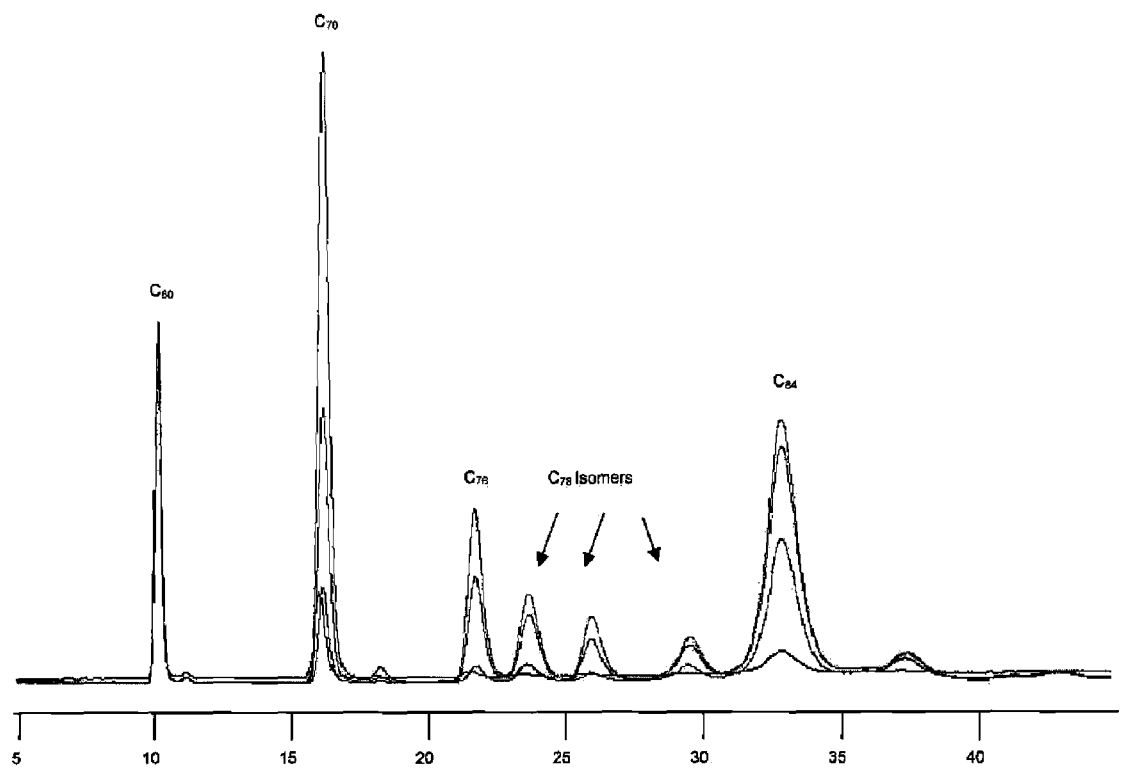
FIG. 6 shows the chromatograms obtained for different single-operation extractions performed with varying extracting agent to fullerite ratios, according to Example 2.d.

As depicted in FIGS. 5 and 6, by varying the weight ratio of extracting agent to fullerite, the method according hereto can be adjusted to the extraction of a selected high-order fullerene.

In conclusion, the extraction method according to the present disclosure allows extracting high-order fullerenes with high purity through simple solid-liquid extractions, avoiding the use of chromatography. Moreover, the method hereof by using compound 1 as the extracting agent allows the extraction of selected high order fullerenes upon varying the ratio of the extracting agent to fullerite.

other cyclic systems and optionally substituted by one or more of the following: alkyl, hydroxyl, protected alcohol functionalities, ether, acyl, carboxylate and alkoxycarbonyl.

2. A compound according to claim 1 of formula Ia:

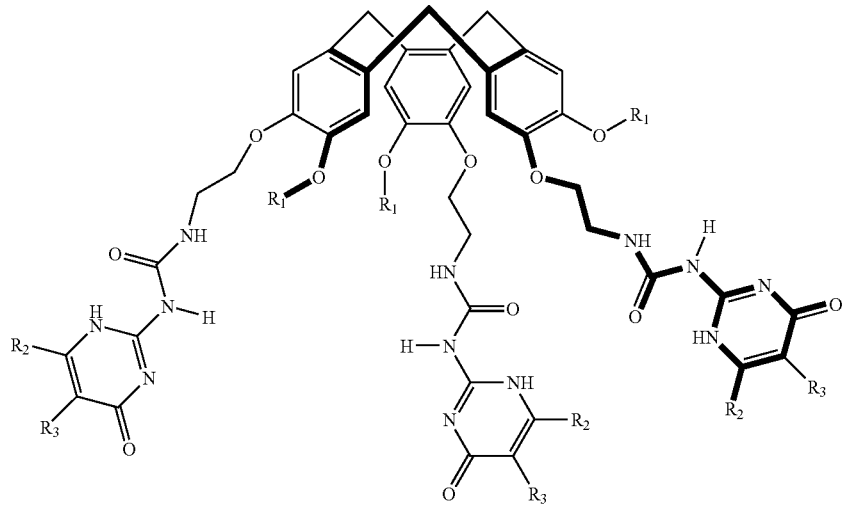

Ia

What is claimed is:

1. A compound of formula I

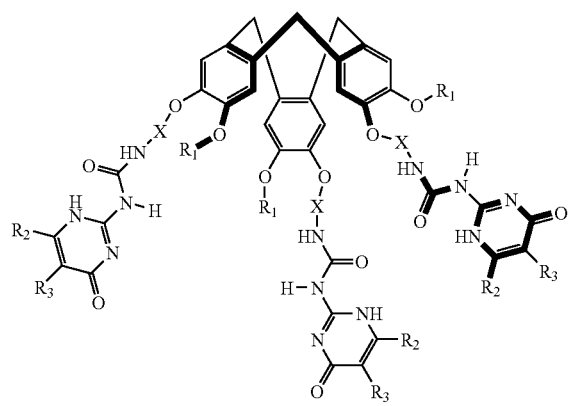

I wherein O—X—NH— is a $C_2$ to $C_5$ alkyl, aryl or benzyl;
$R_1$ is selected from the group comprising linear or branched alkyl and polyethers, optionally unsaturated;
$R_2$ and $R_3$ are selected independently from the group comprising H, hydroxyl, protected alcohol functionalities, ether, acyl, carboxylate, alkoxycarbonyl;
linear or branched alkyl optionally unsaturated and optionally substituted by one or more of the following: carbocycles, heterocarbocycles, aromatic rings, heteroaromatic rings, hydroxyl, protected alcohol functionalities, ether, acyl, carboxylate and akoxycarbonyl;
cycloalkyl, heterocycloalkyl, aryl, heteroaryl, benzyl which are optionally substituted by one or more of the following: alkyl, hydroxyl, protected alcohol functionalities, ether, acyl, carboxylate and alkoxycarbonyl;
or wherein $R_2$ and $R_3$ together form a carbocyclic or heterocyclic group having from 5 to 8 members, optionally fused to other cyclic systems and optionally substituted by one or more of the following: alkyl, hydroxyl, protected alcohol functionalities, ether, acyl, carboxylate and alkoxycarbonyl.

wherein
$R_1$ is selected from the group comprising linear or branched alkyl and polyethers, optionally unsaturated;
$R_2$ and $R_3$ are selected independently from the group comprising H, hydroxyl, protected alcohol functionalities, ether, acyl, carboxylate, alkoxycarbonyl;
linear or branched alkyl optionally unsaturated and optionally substituted by one or more of the following: carbocycles, heterocarbocycles, aromatic rings, heteroaromatic rings, hydroxyl, protected alcohol functionalities, ether, acyl, carboxylate and akoxycarbonyl;
cycloalkyl, heterocycloalkyl, aryl, heteroaryl, benzyl which are optionally substituted by one or more of the following: alkyl, hydroxyl, protected alcohol functionalities, ether, acyl, carboxylate and alkoxycarbonyl;
or wherein $R_2$ and $R_3$ together form a carbocyclic or heterocyclic group having from 5 to 8 members, optionally fused to other cyclic systems and optionally substituted by one or more of the following: alkyl, hydroxyl, protected alcohol functionalities, ether, acyl, carboxylate and alkoxycarbonyl.

3. A compound according to claim 1 wherein
O—X—NH— is selected from the group comprising:

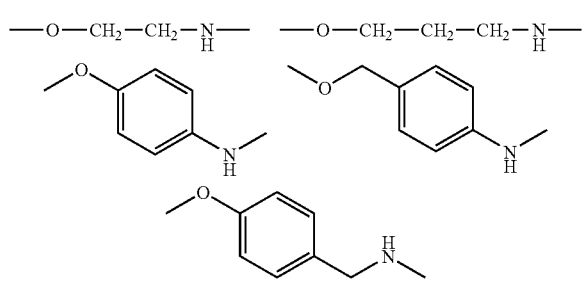

$R_1$ is selected from the group comprising linear or branched alkyl and polyethers, optionally unsaturated;
$R_2$ and $R_3$ are selected independently from the group comprising H, hydroxyl, protected alcohol functionalities, ether, acyl, carboxylate, alkoxycarbonyl;

linear or branched alkyl optionally unsaturated and optionally substituted by one or more of the following: hydroxyl, protected alcohol functionalities, ether, acyl, carboxylate, alkoxycarbonyl, esters and derivatives;
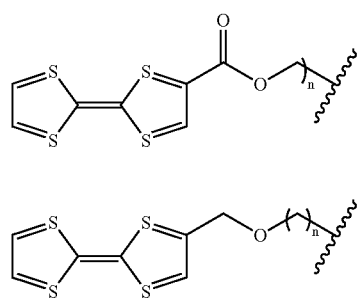
wherein n is an integer from 2 to 4
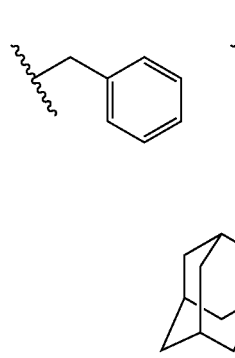
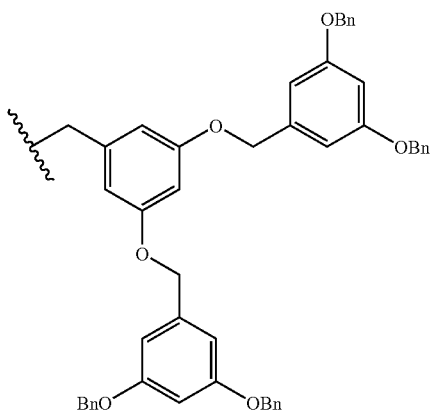
or wherein $R_2$ and $R_3$ together form
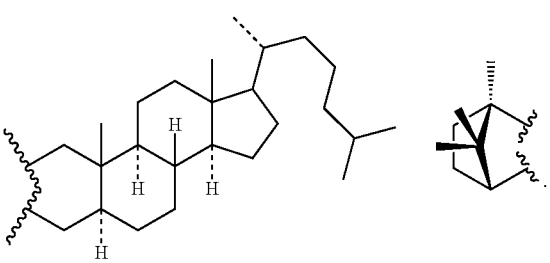
4. A compound according to claim 1 of formula 1:
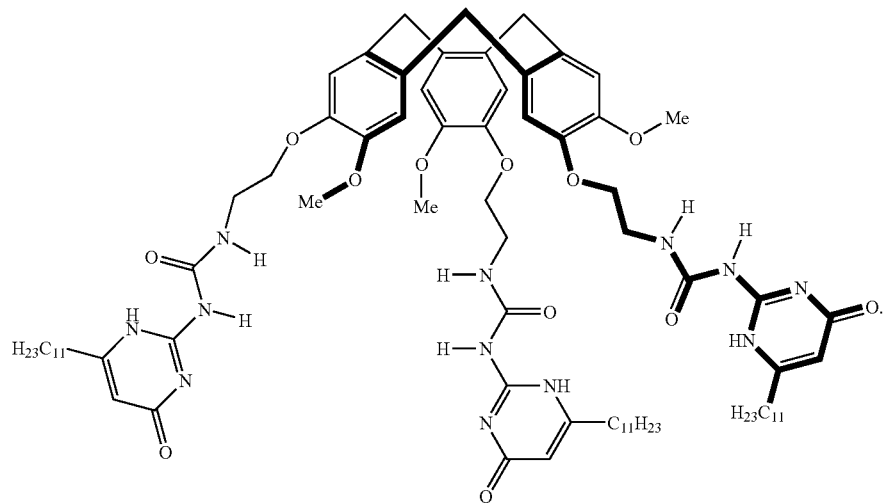
1

5. A compound of formula V

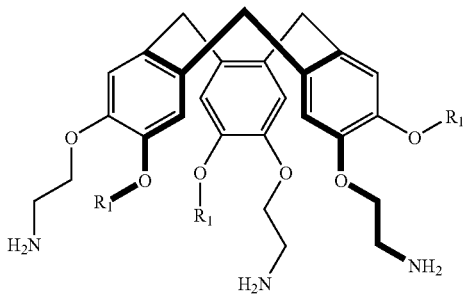

wherein $R_1$ is selected from the group comprising linear or branched alkyl and polyethers, optionally unsaturated.

6. A fullerene-extracting composition comprising a compound according to claim 1.

7. A capsule comprising two units of a compound according to claim 1 non-covalently linked.

8. A non-covalently linked complex comprising a high-order fullerene and two units of a compound according to claim 1.

9. A method for the preparation of a compound of formula Ia according to claim 2 comprising the following operations:
 (a) reacting a CTV-compound of formula IIIa with NaN$_3$ to form the corresponding azide derivative IVa;
 (b) treating the CTV-azide derivative IVa obtained in operation a with triphenylphosphine and ammonia to form a CTV-derivative of formula Va;
 (c) reacting the CTV-derivative of formula Va with an imidazolide of formula IIa.

10. A method for the extraction of high-order fullerenes from a carbonaceous mixture comprising at least one solid-liquid extraction by using a compound of formula I according to claim 1 as extracting agent and a polar aprotic solvent or mixture of solvents as solvent.

11. A method for the extraction of high-order fullerenes from a carbonaceous mixture comprising the following operations:
 (a) contacting the starting mixture in a polar aprotic solvent or mixture of solvents with a selected amount of compound of formula I according to claim 1 and stirring;
 (b) separating the liquid from the solid;
 (c) adding at least one compound selected from the group comprising polar solvents and acids to the liquid;
 (d) isolating the precipitated high-order fullerenes.

12. A method according to claim 11 wherein the polar aprotic solvent or mixture of solvents includes THF or MeCN.

13. A method according to claim 11 further comprising recycling the compound of formula I.

14. A method according to claim 11, wherein the carbonaceous mixture is selected from the group comprising fullerite, soot and mixtures comprising $C_{60}$ and $C_{70}$.

15. A method according to claim 11, wherein the compound of formula I is compound 1

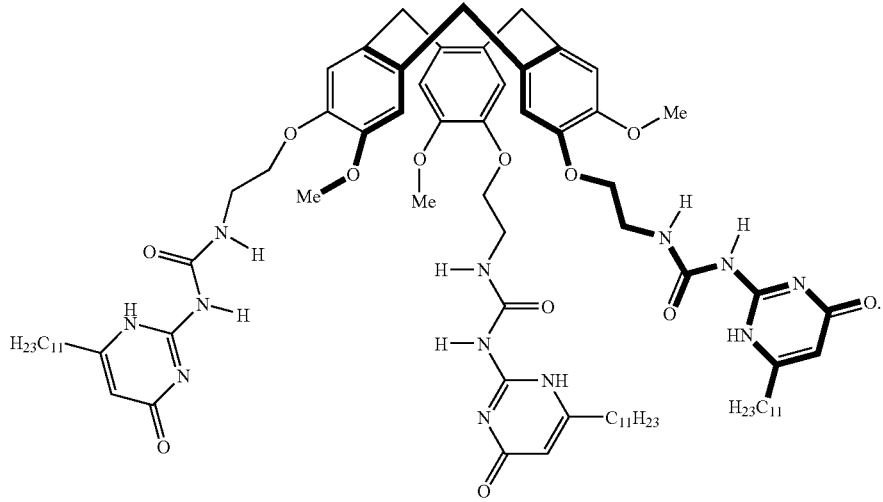

16. A method according to claim 11, wherein the extracted high-order fullerene is $C_{70}$ or $C_{84}$.

17. A method of use of a compound of formula I according to claim 1 as a fullerene-extracting agent; comprising:
 adding a compound of formula I to a carbonaceous mixture and
 extracting a fullerene therefrom.

* * * * *